United States Patent
Pitruzzello et al.

(10) Patent No.: US 9,339,195 B2
(45) Date of Patent: May 17, 2016

(54) APPARATUS, SYSTEM, AND METHOD FOR SEIZURE SYMPTOM DETECTION

(75) Inventors: Ann Pitruzzello, Durham, NC (US); Barbara Kroner, Glenwood, MD (US); Jamie Shorey, Durham, NC (US); David C Strube, Raleigh, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 647 days.

(21) Appl. No.: 13/701,469

(22) PCT Filed: Jan. 27, 2011

(86) PCT No.: PCT/US2011/022757
§ 371 (c)(1),
(2), (4) Date: Jan. 22, 2013

(87) PCT Pub. No.: WO2011/149565
PCT Pub. Date: Dec. 1, 2011

(65) Prior Publication Data
US 2013/0116514 A1   May 9, 2013

Related U.S. Application Data

(60) Provisional application No. 61/349,633, filed on May 28, 2010.

(51) Int. Cl.
*A61B 5/0205*   (2006.01)
*A61B 5/01*   (2006.01)
(Continued)

(52) U.S. Cl.
CPC ........... *A61B 5/02055* (2013.01); *A61B 5/0002* (2013.01); *A61B 5/0026* (2013.01);
(Continued)

(58) Field of Classification Search
CPC .. A61B 5/0205; A61B 5/1118; A61B 5/0402; A61B 5/7275; A61B 5/7282; A61B 5/4094; A61B 5/486; A61B 5/0006; A61B 5/024; A61B 5/0245; A61B 5/04012; A61B 5/4836; A61B 5/04; A61B 5/746; A61B 5/0452; A61B 5/04004; A61B 5/0468; A61B 5/0472; A61B 5/0482; A61B 5/0484; A61B 5/4064; A61B 5/6868; A61B 5/72; A61B 5/00; A61B 5/0004; A61B 5/02; A61B 5/02455; A61B 5/0432; A61B 5/0464; A61B 5/68; G06F 19/3418; G06F 19/30; A61N 1/36064; A61N 1/36135; A61N 1/36585; A61N 1/36139; A61N 1/08; A61N 1/36132; A61N 1/3627; A61M 2230/04; Y10S 128/905; Y10S 128/92; G08B 21/0453; G08B 21/02
See application file for complete search history.

(56) References Cited

U.S. PATENT DOCUMENTS

| 4,586,515 A | 5/1986 | Berger |
|---|---|---|
| 5,573,011 A | 11/1996 | Felsing |

(Continued)

FOREIGN PATENT DOCUMENTS

| WO | 2007142523 A1 | 12/2007 |
|---|---|---|
| WO | 2011159592 A1 | 12/2011 |

(Continued)

OTHER PUBLICATIONS

PCT/US2011/022757, International Search Report & Written Opinion, Jan. 27, 2011.

*Primary Examiner* — Deborah Malamud
(74) *Attorney, Agent, or Firm* — Kunzler Law Group

(57) ABSTRACT

An apparatus, system, and method are disclosed for detecting seizure symptoms in an individual 102. A sensor module 202 receives physiological data for an individual 102 from one or more sensors 110, 112, such as a heart activity sensor. A feature detection module 204 detects a predefined feature 500, 520, 530, 540 in the physiological data. The predefined feature 500, 520, 530, 540 is associated with a seizure or another medical condition. An alert module 206 broadcasts an alert in response to the feature detection module 204 detecting the predefined feature 500, 520, 530, 540.

28 Claims, 7 Drawing Sheets

(51) Int. Cl.

| | | |
|---|---|---|
| *A61B 5/0488* | (2006.01) | |
| *A61B 5/145* | (2006.01) | |
| *A61B 5/04* | (2006.01) | |
| *A61B 5/0402* | (2006.01) | |
| *A61B 5/0432* | (2006.01) | |
| *A61B 5/044* | (2006.01) | |
| *A61B 7/00* | (2006.01) | |
| *A61B 5/00* | (2006.01) | |
| *A61B 5/024* | (2006.01) | |
| *A61B 5/0245* | (2006.01) | |
| *A61B 5/053* | (2006.01) | |
| *A61B 5/08* | (2006.01) | |
| *A61B 5/11* | (2006.01) | |
| *A61B 5/113* | (2006.01) | |

(52) U.S. Cl.
CPC ............... *A61B 5/01* (2013.01); *A61B 5/0205* (2013.01); *A61B 5/0245* (2013.01); *A61B 5/0402* (2013.01); *A61B 5/044* (2013.01); *A61B 5/04012* (2013.01); *A61B 5/0432* (2013.01); *A61B 5/0488* (2013.01); *A61B 5/1112* (2013.01); *A61B 5/1116* (2013.01); *A61B 5/1118* (2013.01); *A61B 5/14542* (2013.01); *A61B 5/4094* (2013.01); *A61B 5/4836* (2013.01); *A61B 5/6801* (2013.01); *A61B 5/6802* (2013.01); *A61B 5/6804* (2013.01); *A61B 5/686* (2013.01); *A61B 5/6831* (2013.01); *A61B 5/6833* (2013.01); *A61B 5/704* (2013.01); *A61B 5/746* (2013.01); *A61B 7/00* (2013.01); *A61B 5/002* (2013.01); *A61B 5/0022* (2013.01); *A61B 5/02438* (2013.01); *A61B 5/02455* (2013.01); *A61B 5/0533* (2013.01); *A61B 5/0816* (2013.01); *A61B 5/1117* (2013.01); *A61B 5/1123* (2013.01); *A61B 5/1135* (2013.01); *A61B 5/4803* (2013.01); *A61B 5/681* (2013.01); *A61B 5/6805* (2013.01); *A61B 5/6891* (2013.01)

(56) References Cited

U.S. PATENT DOCUMENTS

| | | |
|---|---|---|
| 5,810,747 A | 9/1998 | Brudny |
| 6,042,548 A | 3/2000 | Giuffre |
| 6,200,331 B1 | 3/2001 | Swartz |
| 6,315,740 B1 | 11/2001 | Singh |
| 6,482,156 B2 | 11/2002 | Iliff |
| 6,486,779 B1 | 11/2002 | Alroy |
| 6,561,992 B1 | 5/2003 | Eberhart |
| 6,594,524 B2 * | 7/2003 | Esteller et al. .................. 607/45 |
| 7,076,288 B2 | 7/2006 | Skinner |
| 7,146,211 B2 | 12/2006 | Frei |
| 7,167,737 B2 | 1/2007 | Fujii et al. |
| 7,174,206 B2 | 2/2007 | Frei |
| 7,336,187 B2 | 2/2008 | Hubbard, Jr. |
| 2003/0069714 A1 | 4/2003 | Wigley et al. |
| 2006/0235489 A1 | 10/2006 | Drew et al. |
| 2007/0150025 A1 | 6/2007 | Dilorenzo et al. |
| 2007/0167859 A1 | 7/2007 | Finneran et al. |
| 2008/0177194 A1 | 7/2008 | Zhang et al. |
| 2009/0171163 A1 | 7/2009 | Mates et al. |
| 2010/0121215 A1 | 5/2010 | Giftakis et al. |
| 2011/0306845 A1 | 12/2011 | Osorio |
| 2011/0306846 A1 | 12/2011 | Osorio |
| 2012/0226108 A1 | 9/2012 | Osorio |
| 2012/0226168 A1 | 9/2012 | Osorio |
| 2012/0271372 A1 | 10/2012 | Osorio |
| 2013/0096391 A1 | 4/2013 | Osorio |
| 2013/0096393 A1 | 4/2013 | Osorio |
| 2013/0096839 A1 | 4/2013 | Osorio |
| 2013/0096840 A1 | 4/2013 | Osorio |

FOREIGN PATENT DOCUMENTS

| | | |
|---|---|---|
| WO | 2012122066 A1 | 9/2012 |
| WO | 2013056099 A1 | 4/2013 |

\* cited by examiner

APPARATUS, SYSTEM, AND METHOD FOR SEIZURE SYMPTOM DETECTION

BACKGROUND

1. Field of the Invention

This invention relates to medical symptom detection and more particularly relates to seizure symptom detection and warning.

2. Description of the Related Art

Epilepsy and seizures affect nearly three million Americans of all ages, at an estimated annual cost of $15.5 billion in direct and indirect costs. Approximately 200,000 new cases of seizures and epilepsy occur each year. Ten percent of the American population will experience a seizure in their lifetime. Three percent will develop epilepsy by age 75. Annually, approximately five percent of these visit an emergency department due to seizure related injuries, particularly head injuries. Sudden Unexplained Death in Epilepsy Persons ("SUDEP") has an annual incidence as high as one percent in those with risk factors, including long-term uncontrolled generalized tonic-clonic seizures. SUDEP is most often an un-witnessed nocturnal event. Caregivers can provide timely intervention and treatment for some seizures by giving a "rescue" drug, performing cardiopulmonary resuscitation, ("CPR"), or by calling paramedics. However, there is no readily usable device to warn caregivers when a person with epilepsy is having a seizure or an adverse event associated with a seizure, even though people are particularly susceptible to injury while having a seizure.

Typically, Electroencephalography ("EEG"), a measurement of electrical activity along the scalp produced by the firing of neurons within the brain, is used as the primary diagnostic tool to detect a seizure and to diagnose epilepsy. Epileptic activity can create clear abnormalities on a standard EEG study. Physicians depend almost exclusively upon EEG to determine the pre-ictal, ictal, and post-ictal status of a seizure, that is, determining the starting and ending points of a seizure by measuring the beginning and ending of the abnormal brain electrical activity associated with the seizure. In non-clinical settings, an EEG is not a practical sensor for use as a seizure detection device. It is obtrusive, cumbersome, and would not be worn by patients in home, work, or school settings.

SUMMARY OF THE INVENTION

From the foregoing discussion, it should be apparent that a need exists for an apparatus, system, and method that detect seizure symptoms. Beneficially, such an apparatus, system, and method would detect seizure symptoms reliably and unobtrusively, allowing for non-clinical and/or portable use.

The present invention has been developed in response to the present state of the art, and in particular, in response to the problems and needs in the art that have not yet been fully solved by currently available seizure detection methods. Accordingly, the present invention has been developed to provide an apparatus, system, and method for seizure detection that overcome many or all of the above-discussed shortcomings in the art.

The apparatus to detect seizure symptoms is provided with a plurality of modules configured to functionally execute the necessary steps of detecting seizure symptoms. These modules in the described embodiments include a sensor module, a feature detection module, an alert module, a confirmation feature module, a severity module, an adverse event module, a feature personalization module, a data capture module, an activity state module, a treatment module, and a location module.

In one embodiment, the sensor module receives heart activity data for an individual from a heart activity sensor. The sensor module, in a further embodiment, receives additional physiological data for the individual from one or more additional sensors.

In one embodiment, the feature detection module detects a predefined feature in the heart activity data. The predefined feature, in one embodiment, is associated with a seizure. In a further embodiment, the predefined feature is associated with another medical condition. The predefined feature, in one embodiment, includes heart activity outside of predefined heart activity threshold values. In another embodiment, the predefined feature includes a predefined change in heart activity. The predefined feature, in a further embodiment, includes a predefined decrease in heart rate variability.

In one embodiment, the confirmation feature module detects one or more additional predefined features associated with a seizure in additional data for the individual from one or more additional sensors. In a further embodiment, the confirmation feature module detects one or more additional predefined features associated with another medical condition.

In one embodiment, the alert module broadcasts an alert in response to the feature detection module detecting the predefined feature. The alert module, in another embodiment, broadcasts an alert in response to the confirmation feature module detecting the one or more additional predefined features. In an additional embodiment, the alert module broadcasts an initial alert in response to the feature detection module detecting the predefined feature and broadcasts an escalated alert in response to the confirmation feature module detecting the one or more additional predefined features.

In one embodiment, the alert includes information of an estimated severity of a seizure or other medical condition in the individual. The alert module, in another embodiment, broadcasts an adverse event alert in response to the adverse event module detecting a predefined adverse event feature. In one embodiment, the alert module includes information of the location of the individual in an alert. The alert that the alert module broadcasts, in various embodiments, may be an audible alert, a broadcast signal to a caregiver receiver device, a telephonic communication to a medical monitoring center, or the like.

In one embodiment, the one or more additional sensors include a respiration sensor. The one or more additional predefined features, in one embodiment, include a predefined increase in an integrated respiration waveform. In another embodiment, the one or more additional predefined features include a predefined increase in respiration amplitude. The one or more additional predefined features, in a further embodiment, include a predefined change in respiration rate. In one embodiment, the predefined feature includes a breath of at least a predefined duration. In a further embodiment, the one or more additional predefined features include a breath of at least a predefined amplitude. The one or more additional predefined features, in another embodiment, include a breath of at least a predefined volume. The one or more additional predefined features, in one embodiment, include a predefined change in a period of a respiration interval.

The one or more additional sensors, in one embodiment, include an electromyography ("EMG") sensor that measures muscle activity in the individual. The one or more additional predefined features, in one embodiment, include a predefined change in magnitude of an integrated EMG waveform. In another embodiment, the one or more additional predefined features include a predefined increase in rhythmic muscle activity. In a further embodiment, the one or more additional predefined features include a predefined increase in mean firing rate of a muscle. The one or more additional predefined features, in another embodiment, includes a predefined change in an accumulated EMG waveform within a predefined time window. In an additional embodiment, the one or more additional predefined features include a predefined decrease in signal energy of an EMG waveform preceding the predefined feature.

In a further embodiment, the one or more additional sensors further include the EMG sensor and an opposing EMG sensor. The EMG sensor, in one embodiment, measures muscle activity in a first muscle group and the opposing EMG sensor measures muscle activity in an opposing muscle group. The one or more additional predefined features, in one embodiment, comprise a predefined amount of correlation between muscle activity in the first muscle group and in the opposing muscle group.

In one embodiment, the one or more additional sensors include a skin conductivity sensor. The one or more additional predefined features, in one embodiment, include a predefined increase in a skin conductivity of the individual. In a further embodiment, the one or more additional sensors include a skin temperature sensor. The one or more additional predefined features, in one embodiment, include a predefined change in a skin temperature of the individual. In another embodiment, the one or more additional sensors include a peripheral blood oxygen saturation sensor. The one or more additional predefined features, in one embodiment, include a predefined decrease in a peripheral blood oxygen level of the individual. In an additional embodiment, the one or more additional sensors include an audible noise sensor. The one or more additional predefined features, in one embodiment, includes a predefined audible vocalization by the individual.

In one embodiment, the severity module determines an estimated severity of a seizure in the individual. The estimated severity, in one embodiment, is based on a combination of a weighted severity value associated with the predefined feature and one or more weighted severity values associated with the one or more additional predefined features. In one embodiment, the one or more additional sensors include a body motion sensor that measures motion, orientation, or the like of the individual. The severity module, in one embodiment, bases the estimated severity of a seizure in the individual at least partially on input from the body motion sensor. The body motion sensor, in various embodiments, may include a gyroscope, an accelerometer, a gravity sensor, or the like.

In one embodiment, the adverse event module detects a predefined adverse event feature in the heart activity data and/or in the data from the one or more additional sensors. The predefined adverse event feature, in one embodiment, is associated with an adverse event such as a fall, an arrhythmia, respiratory distress, a cessation of breathing, or a loss of consciousness.

In one embodiment, the feature personalization module adjusts a definition of the predefined feature based on heart activity data and/or other physiological data from one or more previous seizures of the individual. The activity state module, in one embodiment, detects an activity state of the individual and adjusts a definition of the predefined feature based on the detected activity state.

In one embodiment, the treatment module dispenses a treatment to the individual in response to the feature detection module detecting the predefined feature. The location module, in one embodiment, determines a location of the individual, and the alert module includes information of the location of the individual in an alert. The data capture module, in one embodiment, stores at least the heart activity data associated with the predefined feature.

A system of the present invention is also presented to detect seizure symptoms. The system may be embodied by a heart activity sensor, a securing article, and a controller. In particular, the system, in one embodiment, includes one or more additional sensors, a caregiver receiver device, a base unit device, and a power storage device.

The heart activity sensor, in one embodiment, measures a heart rate of an individual. The securing article, in a further embodiment, removably places the heart activity sensor in proximity to the individual. The power storage device, in one embodiment, provides electric power to the heart activity sensor and/or the controller. The power storage device, in one embodiment, is coupled to the securing article. In a further embodiment, the controller is coupled to the securing article.

The securing article, in one embodiment, includes a wearable strap coupled to the heart activity sensor. In a further embodiment, the securing article includes an article of clothing to which the heart activity sensor is coupled. In another embodiment, the securing article includes an article of jewelry to which the heart activity sensor is coupled. The securing article, in one embodiment, includes a bedding layer to which the heart activity sensor is coupled. In an additional embodiment, the securing article includes an adhesive bandage that affixes the heart activity sensor to the individual. In another embodiment, the securing article includes an implanted device that implants the heart activity sensor within the individual.

The controller, in one embodiment, includes one or more of the modules discussed above with regard to the apparatus of the present invention. In one embodiment, the controller includes a sensor module that receives heart activity data for the individual from the heart activity sensor. In a further embodiment, the controller includes a feature detection module that detects a predefined feature in the heart activity data that is associated with a seizure or other medical condition. The controller, in another embodiment, includes an alert module that broadcasts an alert in response to the feature detection module detecting the predefined feature.

The one or more additional sensors, in one embodiment, measure physiological data of the individual. The securing article, in one embodiment, removably places the one or more additional sensors in proximity to the individual. The controller, in one embodiment, includes a confirmation feature module that detects one or more additional predefined features associated with a seizure in data from the one or more additional sensors. The sensor module, in one embodiment, receives the data from the one or more additional sensors. The alert module, in a further embodiment, broadcasts the alert in response to the confirmation feature module detecting the one or more additional predefined features.

The caregiver receiver device, in one embodiment, receives the alert from the alert module. The base unit device, in one embodiment, stores at least a portion of the heart activity data and/or the physiological data. In a further embodiment, the base unit device visually displays at least a portion of the heart activity data. The base unit device, in another embodiment, sends at least a portion of the heart activity data to a remote device.

A method of the present invention is also presented for detecting seizure symptoms. The method in the disclosed embodiments substantially includes the steps necessary to carry out the functions presented above with respect to the operation of the described apparatus and system. In one embodiment, the method includes receiving heart activity data for an individual from a heart activity sensor. The method, in a further embodiment, includes detecting a predefined feature in the heart activity data associated with a seizure. In another embodiment, the method includes broadcasting an alert in response to detecting the predefined feature.

The method, in one embodiment, includes receiving additional data for the individual from one or more additional sensors. In a further embodiment, the method includes detecting one or more additional predefined features associated with a seizure in the additional data from the one or more additional sensors. Broadcasting the alert, in one embodiment, is in response to detecting the predefined feature and detecting the one or more additional predefined features.

In one embodiment, the method includes determining an estimated severity of a seizure in the individual. Determining the estimated severity, in one embodiment, is based on a combination of a weighted severity value associated with the predefined feature and one or more weighted severity values associated with the one or more additional predefined features. The alert, in one embodiment, includes information of the estimated severity.

In a further embodiment, the method includes detecting a predefined adverse event feature in the heart activity data and/or the additional data from the one or more additional sensors. The predefined adverse event feature, in one embodiment, is associated with an adverse event such as a fall, an arrhythmia, respiratory distress, a cessation of breathing, or a loss of consciousness. The method, in another embodiment, includes broadcasting an adverse event alert in response to detecting the predefined adverse event feature.

In one embodiment, the method includes adjusting a definition of the predefined feature based on heart activity data or other physiological data from one or more previous seizures of the individual. In another embodiment, the method includes detecting an activity state of the individual. The method, in a further embodiment, includes adjusting a definition of the predefined feature based on the detected activity state.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
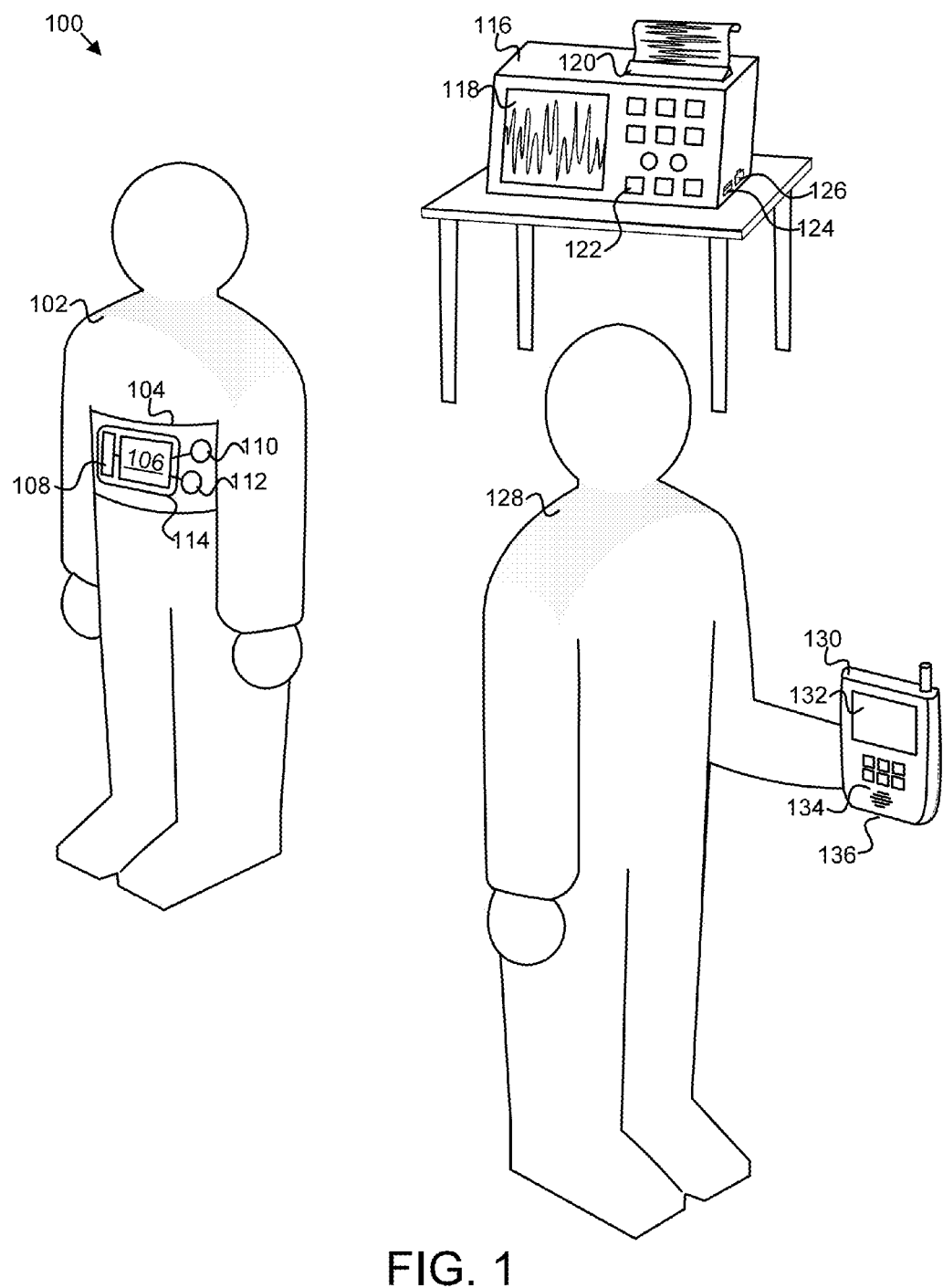
FIG. 1 is a schematic block diagram illustrating one embodiment of a system for seizure symptom detection in accordance with the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the software portions are stored on one or more computer readable mediums.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing.

More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Aspects of the present invention are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and computer instructions.

FIG. 1 depicts one embodiment of a system 100 for seizure symptom detection. In the depicted embodiment, the system 100 includes a controller 106 that receives data from one or more sensors 110, 112. In the depicted embodiment, a power storage device 108 powers the controller 106, a housing 114 encases the controller 106 and the power storage device 108, and a securing article 104 secures the housing 114, the controller 106, the power storage device 108, and the one or more sensors 110, 112 to an individual 102. The system 100, in the depicted embodiment, further includes a base station 116 and a caregiver receiver device 130.

In general, the system 100 uses the one or more sensors 110, 112 to measure physiological data of the individual 102, detects features in the physiological data associated with a seizure or other medical condition, and broadcasts an alert to a caregiver 128. In one embodiment, the one or more sensors 110, 112 are relatively noninvasive, and measure one or more secondary indications of a seizure, such as heart activity/rate, respiration, muscle activity, skin conductivity, skin temperature, blood oxygen saturation, body orientation, body motion, audible vocalizations, and the like instead of using uncomfortable and often invasive electroencephalography ("EEG") sensors to measure electrical activity in the brain directly.

The system 100, in various embodiments, may be used in a home setting, in a clinical setting, in a work setting, in an educational setting, in a portable setting, or the like. The one or more sensors 110, 112, in various embodiments, may be integrated into clothing, jewelry, bedding, or another item to provide noninvasive, unobtrusive, child-safe, comfortable, and/or aesthetically pleasing use of the system 100 for the individual 102. In one embodiment, the system 100 detects symptoms of several different types of seizures, such as tonic-clonic seizures, myoclonic seizures, infantile spasms, tonic seizures, atonic/drop seizures, and/or other types of seizures. In various embodiments, the system 100 may be used to document the effectiveness of a treatment plan, to prevent seizure-related injuries and deaths, to improve health outcomes and quality of life for people with epilepsy and their families, to reduce the cost of treatment, and the like. In a further embodiment, in addition to or instead of detecting seizure symptoms, the system 100 may detect and warn of cardiac or respiratory distress, falling down, vomiting, pyrexia, sleep apnea, night terrors, sleepwalking, other sleep disturbances, fear, and/or other medical conditions.

The controller 106, in the depicted embodiment, is in communication with the one or more sensors 110, 112. In general, the controller 106 receives data for the individual 102 from the one or more sensors 110, 112, detects one or more predefined features in the data for the individual that are associated with a seizure, and broadcasts an alert in response to detecting the one or more predefined features. Embodiments of the controller 106 are described in greater detail with regard to FIG. 2 and FIG. 3.

The controller 106, in one embodiment, includes a data processing apparatus, such as a processor, a microcontroller, an application specific integrated circuit ("ASIC"), a digital signal processor ("DSP"), a programmable hardware device, a field programmable gate array ("FPGA"), or the like. The controller 106, in a further embodiment, includes volatile memory data storage, non-volatile data storage, or another type of computer-readable storage medium for storing computer executable code, data from the one or more sensors 110, 112, and the like. The controller 106, in one embodiment, is dedicated exclusively to performing the functions of the system 100. In a further embodiment, the controller 106 is part of a portable computing device, such as a mobile telephone, a tablet computer, a mobile communications device, a mobile entertainment device, or the like, that includes a software application for performing the functions of the system 100.

In the depicted embodiment, the controller 106 is disposed with the one or more sensors 110, 112, in close proximity to the individual 102. In a further embodiment, the controller 106 may be included in the base station 116, the caregiver receiver device 130, or may otherwise be disposed at an offset from the individual 102. In other embodiments, portions of the controller 106 and/or functionality of the controller, such as the modules discussed below with regard to FIGS. 2 and 3, may be distributed between different devices and/or locations, such as a hardware controller 106 coupled to the securing article 104, the base station 116, the caregiver receiver device 130, and/or other devices. The controller 106, in the depicted embodiment, is coupled to the one or more sensors 110, 112 with a direct wire-line connection. In a further embodiment, the one or more sensors 110, 112 may wirelessly transmit data to the controller 106 using RF or infrared communications, such as Bluetooth, Wi-Fi, wireless broadband, ZigBee, Z-wave, ultra-wideband ("UWB"), infrared data association ("IrDA") communications, and the like.

In one embodiment, the one or more sensors 110, 112 each measure a particular type of physiological data of the individual 102. The one or more sensors 110, 112, in various embodiments, may include a heart activity sensor, a respiration sensor, a muscle activity sensor, a skin temperature sensor, a skin conductivity sensor, a peripheral blood oxygen saturation sensor, an audible vocalization sensor, a body motion sensor, and/or other types of physiological sensors. In one embodiment, several different sensors 110, 112 may share electrodes, leads, or other components. For example, in one embodiment, an electrocardiogram ("EKG" or "ECG") heart activity sensor may share one or more electrodes with an electromyography ("EMG") muscle activity sensor, or the like.

In the depicted embodiment, the one or more sensors 110, 112 include multiple sensors 110, 112. Including multiple types of sensors 110, 112, in one embodiment, reduces false positives in the system 100 without decreasing sensitivity of the system 100. In one embodiment, the one or more sensors 110, 112, include a heart activity sensor 110 that measures heart activity data for the individual 102 and one or more additional sensors 112 that measure additional physiological data for the individual 102. The one or more additional sensors 112 may include a respiration sensor, a muscle activity sensor, a skin temperature sensor, a skin conductivity sensor, a peripheral blood oxygen saturation sensor, an audible vocalization sensor, a body motion sensor, and/or other types of physiological sensors. In a further embodiment, sensors 110, 112 may be added or removed from the system 100 to customize the system 100 to the individual 102.

In one embodiment, the power storage device 108 provides electric power to one or more of the sensors 110, 112 and the controller 106. In the depicted embodiment, the power storage device is coupled to the securing article 104 with the controller 106 and the one or more sensors 110, 112. In a further embodiment, the power storage device 108 may include several power storage devices 108, with one or more power storage devices 108 located with the one or more sensors 110, 112, and one or more power storage devices 108 located with the controller 106, which may be disposed at a location that is remote from the one or more sensors 110, 112. The power storage device 108, in various embodiments, may include one or more batteries, one or more fuel cells, and/or another type of power storage device. The power storage device 108, in one embodiment, is rechargeable. In a further embodiment, the controller 106 and/or the one or more sensors 110, 112 receive electric power from another electric power source, such as mains electric power, a power supply unit ("PSU"), or the like.

In one embodiment, the housing 114 encases one or more components of the system 100, such as the controller 106, the power storage device 108, the one or more sensors 110, 112, and/or other components of the system 100. The housing 114, in one embodiment, protects enclosed components from damage due to external factors, such as mechanical pressure, liquids, and the like. In one embodiment, the housing 114 is formed of one or more durable materials, such as plastics, metals, composite materials, and the like. The housing 114, in the depicted embodiment, is coupled to the securing article 104, to provide mechanical support for the controller 106 and the power storage device 108. In a further embodiment, the housing 114 provides mechanical support for one or more of the sensors 110, 112.

In one embodiment, the securing article 104 removably places the one or more sensors 110, 112 in proximity to the individual 102. In a further embodiment, the securing article 104 may include several separate securing articles for placing different sensors 110, 112 at different positions relative to the individual 102, such as around the chest, around an arm, around a leg, implanted within the individual 102, or the like. In various embodiments, the securing article 104 may include one or more wearable straps coupled to the sensors 110, 112, articles of clothing to which the sensors 110, 112 are coupled, articles of jewelry to which the sensors 110, 112 are coupled, bedding layers to which the sensors 110, 112 are coupled, adhesive bandages that affix the sensors 110, 112 to the individual 102, one or more implanted devices that implant the sensors 110, 112 within the individual 102, and/or other securing articles. The securing article 104, in one embodiment, is designed to be relatively small, unobtrusive, comfortable, and/or attractive, to encourage use by the individual 102 and to facilitate use of the system 100 in a variety of settings.

In one embodiment, the base station 116 interfaces with the controller 106 to provide one or more additional functions. In the depicted embodiment, the base station 116 includes a display 118, a printing interface 120, user inputs 122, a device interface 124, and a network interface 126. The base station 116, in one embodiment, stores at least a portion of the data from the one or more sensors 110, 112 in a computer-readable storage medium. For example, in one embodiment, the base station 116 stores data from the one or more sensors 110, 112 corresponding to a predefined feature associated with a seizure.

In a further embodiment, the base station 116 visually displays at least a portion of the data from the one or more sensors 110, 112 on the display 118. The base station 116, in various embodiments, may display sensor data directly from the one or more sensors 110, 112, sensor data received from the controller 106, sensor data retrieved from a computer-readable storage medium of the base station 116, or the like. The display 118, in various embodiments, may include a liquid crystal display ("LCD"), a light emitting diode ("LED") display, a cathode ray tube ("CRT") display, or another type of electronic display.

In one embodiment, the base station 116 prints at least a portion of the data from the one or more sensors 110, 112 using the printing interface 120. The printing interface 120, in various embodiments, may include a printer that is integrated with the base station 116; a universal serial bus ("USB") port, a serial port, or the like for connecting a printer to the base station 116; and/or another type of printing interface.

In one embodiment, the device interface 124 provides communications between the controller 106 and the base station 116. The device interface 124, in the depicted embodiment, includes a port, such as a USB port, a serial port, an IEEE 1394 ("FireWire") port, or the like. In a further embodiment, the device interface 124 includes a wireless link between the controller 106 and the base station 116, such as the RF or infrared wireless communications described above with regard to the one or more sensors 110, 112. In one embodiment, the controller 106 communicates data from the one or more sensors 110, 112 to the base station 116 using the device interface 124. In a further embodiment, the device interface 124 provides electric power to charge the power storage device 108 while the controller 106 is connected to the device interface 124.

In one embodiment, the network interface 126 allows the base station 116 to communicate over a communications network, such as a local area network ("LAN"), a wide area network ("WAN"), the Internet, or the like. The network interface 126, in the depicted embodiment, includes a wired Ethernet port. In a further embodiment, the network interface 126 includes a wireless network interface, such as Wi-Fi, wireless broadband, or the like, or includes a different type of wired network interface. The base station 116, in one embodiment, sends at least a portion of the data from the one or more sensors 110, 112 to a remote device using the network interface 126. In one embodiment, the base station 116 sends data from the one or more sensors 110, 112 to a doctor or other medical professional using the network interface 126.

In one embodiment, the user inputs 122 allow a user, such as the individual 102 or the caregiver 128 to interact with the base station 118. Examples of user inputs 122 include buttons, keys, knobs, dials, switches, and the like. The user inputs 122, in various embodiments, allow a user to select data from the one or more sensors 110, 112 for display or printing, to input settings for the system 100, to upload data using the network interface 126, and/or otherwise interact with the base station 118.

In one embodiment, the caregiver receiver device 130 receives alerts from the controller 106 and relays the alerts to the caregiver 128. In the depicted embodiment, the caregiver receiver device 130 includes a display 132, user inputs 134, and a speaker 136. The caregiver 128, in one embodiment, is a responsible individual who can assist the individual 102 in case of a seizure or other medical condition. Examples of possible caregivers 128 include parents, family members, doctors, nurses, other medical professionals, neighbors, educators, work colleagues, and the like. The caregiver receiver device 130 uses the speaker 136 and/or the display 132 to alert the caregiver 128 of detected seizure symptoms in the individual 102 in response to receiving an alert from the controller 106.

The controller 106 and the caregiver receiver device 130, in one embodiment, communicate wirelessly using RF or other wireless communications, such as Bluetooth, Wi-Fi, wireless broadband, ZigBee, Z-wave, UWB, and the like. In a further embodiment, the controller 106 and the caregiver device 130 communicate using wired communications over a wired data network, using a direct wire-line connection, or the like. Wireless communications between the controller 106 and the caregiver receiver device 130 facilitate mobile, portable use, while in other embodiments, the controller 106 may be integrated with the caregiver receiver device 130, installed in a clinical setting for non-mobile use, or used in another setting where wired communications may be convenient.

The caregiver receiver device 130, in one embodiment, emits one or more audible and/or visual alerts to the caregiver 128 in response to receiving an alert from the controller 106. For example, the caregiver receiver device 130 may use the speaker 136 to sound an audible alert to the caregiver 128, use one or more lights to visually alert the caregiver 128, display a visual alert to the caregiver 128 on the display 132, and/or otherwise alert the caregiver 128.

In one embodiment, the caregiver receiver device 130 uses the display 132 to provide information of the detected seizure symptoms in the individual 102 to the caregiver 128. The controller 106, in one embodiment, broadcasts an alert to the caregiver receiver device 130 that includes information of the detected seizure symptoms, such as an estimated severity, detected seizure features, data from the one or more sensors 110, 112, a detected location of the individual 102, and/or other information. In one embodiment, the user inputs 134 allow the caregiver 128 to navigate information on the display 132, request that the caregiver receiver device 130 display additional information, end one or more aspects of the alert, input one or more settings for the caregiver receiver device 130 and/or for the system 100, and the like.

Figure 2:
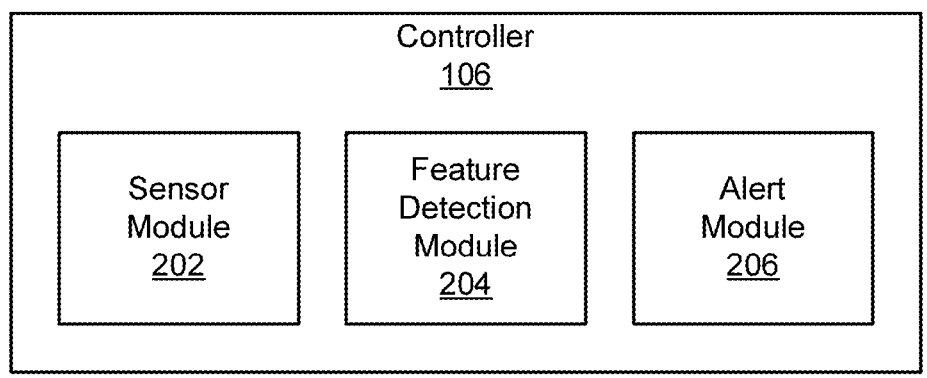
FIG. 2 is a schematic block diagram illustrating one embodiment of a controller for seizure symptom detection in accordance with the present invention.

FIG. 2 depicts one embodiment of the controller 106 for seizure symptom detection. The controller 106, in one embodiment, is substantially similar to the controller 106 described above with regard to FIG. 1. In the depicted embodiment, the controller 106 includes a sensor module 202, a feature detection module 204, and an alert module 206.

In one embodiment, the sensor module 202 receives data for the individual 102 from the one or more sensors 110, 112. The sensor module 202, in one embodiment, receives heart activity data for the individual 102 from the heart activity sensor 110. In a further embodiment, the sensor module 202 receives additional physiological data for the individual 102 from the one or more additional sensors 112. The sensor module 202, in another embodiment, receives both heart activity data for the individual 102 from the heart activity sensor 110 and additional physiological data for the individual 102 from the one or more additional sensors 112. As described above with regard to FIG. 1, in various embodiments, the one or more sensors 110, 112 may include a heart activity sensor, a respiration sensor, a muscle activity sensor, a skin temperature sensor, a skin conductivity sensor, a peripheral blood oxygen saturation sensor, an audible vocalization sensor, a body motion sensor, and/or other types of physiological sensors.

In one embodiment, the feature detection module 204 detects one or more predefined features in the sensor data that the sensor module 202 receives. The feature detection module 204, in one embodiment, detects one or more predefined features that are associated with a seizure. In a further embodiment, the feature detection module 204 detects predefined features associated with one or more other types of medical conditions, such as cardiac or respiratory distress, falling down, vomiting, pyrexia, sleep apnea, night tenors, sleepwalking, other sleep disturbances, fear, and/or other medical conditions. A predefined feature, as used herein, is a property of data from a sensor 110, 112 that is designated as a possible indicator of a seizure or another medical condition.

In one embodiment, the controller 106 adjusts definitions of the one or more predefined features based on an activity level of the individual 102, based on previous seizures or other medical conditions in the individual 102, based on user input, or the like. Adjusting definitions for predefined features is described in greater detail below with regard to the feature personalization module 308 and the activity state module 312 of FIG. 3.

In one embodiment, the alert module 206 broadcasts one or more alerts in response to the feature detection module 204 detecting a predefined feature. In a further embodiment, the alert module 206 broadcasts one or more alerts in response to the feature detection module 204 detecting a first predefined feature from one sensor 110, 112 and the feature detection module 204 (or a confirmation feature module 302, discussed below with regard to FIG. 3) detecting one or more additional predefined features from a different sensor 110, 112. In another embodiment, the alert module 206 broadcasts one or more alerts in response to a combination of weighted severity values associated with one or more detected predefined features exceeding a predefined threshold, or the like. For example, in one embodiment, each predefined feature may be assigned a weighted severity value, a range of weighted severity values based on a measured aspect of a detected feature, or the like, and the alert module 206 may combine weighted severity values from several detected predefined features to determine when to broadcast an alert.

The alert module 206, in one embodiment, broadcasts an audible and/or visual alert locally in the vicinity of the individual 102. In a further embodiment, the alert module 206 broadcasts an alert signal to the caregiver receiver device 130. In another embodiment, the alert module 206 broadcasts a communication, such as a telephonic or data communication, to a medical monitoring center to alert a medical professional. The alert module 206, in one embodiment, broadcasts an alert that includes information of detected features, such as the sensor 110, 112 used to detect each detected feature, an estimated severity of a seizure or other medical condition in the individual 102 based on detected features, data associated with detected features, or the like.

In one embodiment, the alert module 206 broadcasts several levels or types of alerts. The alert module 206, in one embodiment, broadcasts an initial alert in response to the feature detection module 204 detecting a first predefined feature and broadcasts an escalated alert in response to the feature module 204 (or a confirmation feature module 302 as described below) detecting one or more additional predefined features. In a further embodiment, the alert module 206 broadcasts an adverse event alert in response to the controller 106 detecting a predefined adverse event feature indicating that an adverse event associated with a seizure, such as a fall, an arrhythmia, respiratory distress, a cessation of breathing, a loss of consciousness, and the like, may have occurred. Adverse event detection is discussed in greater detail below with regard to the adverse event module 306 of FIG. 3.

Figure 3:
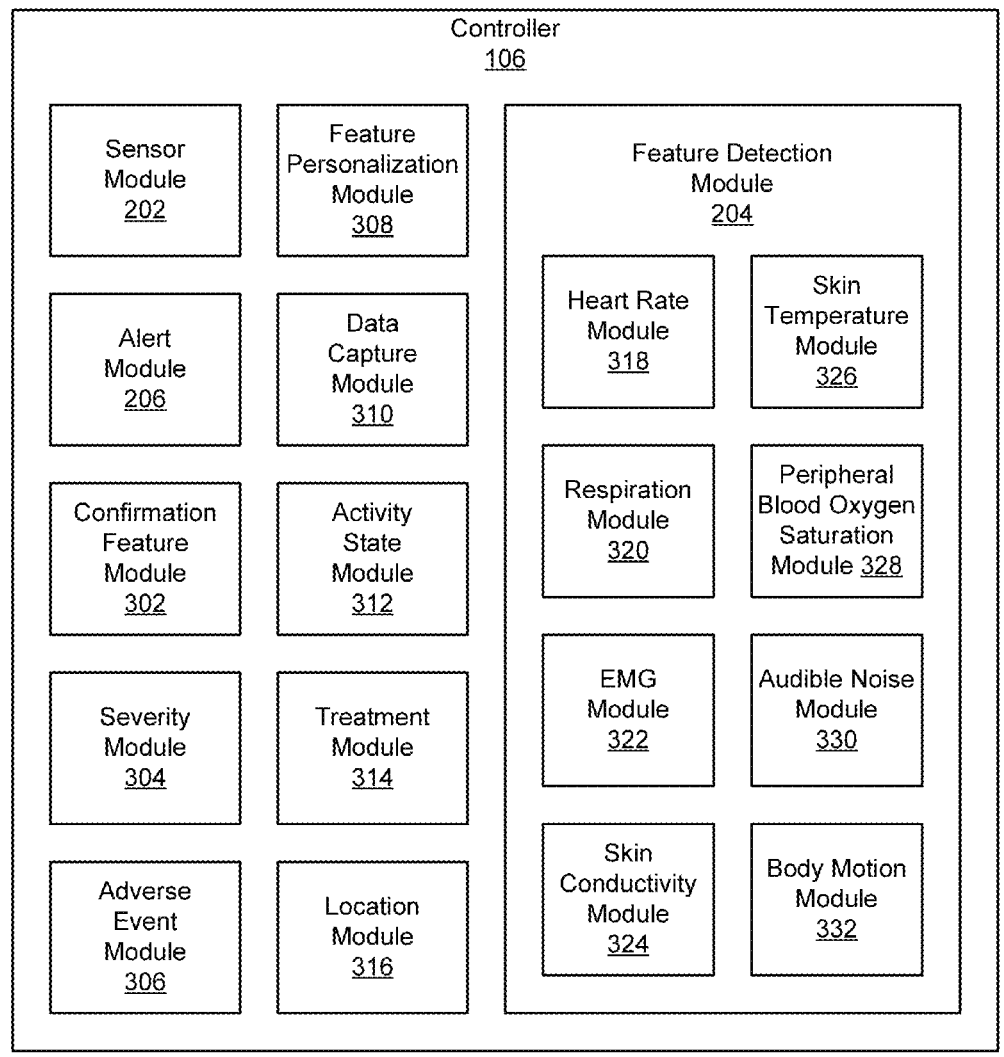
FIG. 3 is a schematic block diagram illustrating another embodiment of a controller for seizure symptom detection in accordance with the present invention.

FIG. 3 is a schematic block diagram illustrating another embodiment of the controller 106 for seizure symptom detection. The controller 106, in one embodiment, is substantially similar to the controller 106 described above with regard to FIG. 1 and/or with regard to FIG. 2. In the depicted embodiment, the controller 106 includes the sensor module 202, the feature detection module 204, the alert module 206, and further includes a confirmation feature module 302, a severity module 304, an adverse event module 306, a feature personalization module 308, a data capture module 310, an activity state module 312, a treatment module 314, and a location module 316. The feature detection module 204, in the depicted embodiment, includes a heart activity module 318, a respiration module 320, an electromyography ("EMG") module 322, a skin conductivity module 324, a skin temperature module 326, a peripheral blood oxygen saturation module 328, an audible noise module 330, and a body motion module 332. In other embodiments, the feature detection module 204 includes a subset of the depicted modules.

In one embodiment, the heart activity module 318 detects a predefined feature in heart activity data from a heart activity sensor 110. Heart activity data, in various embodiments, may include a heart rate, an instantaneous heart rate, an R wave to R wave ("R-R") interval, or the like. Examples of predefined features in heart activity data that are associated with a seizure (or another medical condition) include heart activity/rate outside of predefined heart activity threshold values, a predefined change in heart activity, a predefined decrease in heart rate variability ("HRV"), and the like. The heart activity sensor 110, in one embodiment, includes an EKG sensor, or the like. In a further embodiment, the heart activity sensor 110 includes a single lead EKG sensor, with two or three electrodes. In another embodiment, the heart activity sensor 110 includes a pulse oximeter that measures heart activity and may also measure peripheral blood oxygen saturation.

During a seizure, individuals 102 often experience an abnormally rapid rise in heart activity/rate, which the heart activity module 318 detects. The heart activity module 318, in one embodiment, processes time series data from the heart activity sensor 110 to measure an instantaneous heart rate of the individual 102 and a rate of change in the instantaneous heart rate of the individual 102. The instantaneous heart rate may be measured from an R-R interval determined from the heart activity data, from an inter-beat interval determined from the heart activity data, or the like. For example, in one embodiment, the heart activity module 318 calculates the rate of change by taking the absolute value of the derivative of the instantaneous heart rate as a function of time.

In one embodiment, a predefined feature that the heart activity module 318 detects in the heart activity data is heart activity of the individual 102, such as a heart rate, exceeding a threshold value. The threshold value for the heart activity, in one embodiment, is a heart rate exceeding about between 110 bpm and 150 bpm for a person over the age of about three years old, or the like. In a further embodiment, the threshold value for the heart activity is a heart rate exceeding about 125 bpm for a person over the age of about three years old. The threshold value for the heart activity, in certain embodiments, is a heart rate exceeding a threshold percentage of a maximum heart rate for the individual 102. Due to differences in maximum heart rate for individuals 102 of different ages, a threshold value for heart activity may be higher for infants and young children than for adults. In one embodiment, the heart activity module 318 assigns heart rates above the selected threshold value increasing weighted severity values.

In one embodiment, a predefined feature that the heart activity module 318 detects in the heart activity data is a rate of change in the heart rate or other heart activity of the individual 102 exceeding a threshold value. The threshold value for the rate of change in the heart rate, in one embodiment, is a rate of change exceeding about between 300 and 1500 bpm$^2$. In a further embodiment, the threshold value for the rate of change in the heart rate is a rate of change exceeding about 500 bpm$^2$. A threshold value for the rate of change of a heart rate or other heart activity, in certain embodiments, may be selected based on an age of the individual 102, or the like. In one embodiment, the heart activity module 318 assigns changes in the heart rate above the selected threshold value increasing weighted severity values. In another embodiment, a predefined feature that the heart activity module 318 detects in the heart activity data is both the heart rate of the individual 102 and the rate of change in the heart rate exceeding threshold values.

In one embodiment, a decrease in HRV, the variability in the time interval between heart beats, is a predefined feature that the heart activity module 318 detects in the heart activity data of the individual 102. In a further embodiment, the heart activity module 318 detects a decrease in HRV as a predefined feature to detect a risk of an adverse event during or following a seizure, as a decrease in HRV associated with a seizure is also associated with an increased risk of SUDEP. In a further embodiment, the heart activity module 318 detects a decrease in HRV as a predefined feature for a different medical condition, such as congestive heart failure, diabetic neuropathy, infant distress, or the like. The heart activity module 318, in various embodiments, may use a time-domain analysis, a frequency-domain analysis, a non-linear analysis, or the like to detect a decrease in HRV in the heart rate of the individual 102. In a further embodiment, the heart activity module 318 detects additional predefined features in the heart activity of the individual 102 that are associated with a seizure or another medical condition.

In one embodiment, the respiration module 320 detects one or more predefined features in data from a respiration sensor 112. The respiration sensor 112, in one embodiment, includes a respiration belt or chest strap that measures chest expansion and contraction during breaths of the individual 102. In another embodiment, an EKG sensor or other heart activity sensor 110 is configured to measure heart activity of the individual 102 and to measure respiration of the individual 102, integrating the heart activity sensor 110 and the respiration sensor 112 into a single sensor. In a further embodiment, the respiration sensor 112 includes an acoustic transducer that measures respiration, or another sensor that measures respiration.

During a seizure, individuals 102 often experience a single long breath or a single long cessation of breathing at or shortly before other signs of a seizure, and often experience rapid, labored breathing after the single long breath or cessation of breathing. Similarly, a respiration rate of an individual 102 often increases during a seizure. The respiration module 320, in one embodiment, detects predefined features in data from the respiration sensor 112 that are associated with a seizure or another medical condition, including one or more of a predefined increase in an integrated respiration waveform, a predefined increase in respiration amplitude, a predefined change in respiration rate, a breath of at least a predefined duration, a breath of at least a predefined amplitude, a breath of at least a predefined volume, a predefined change in a period of a respiration interval, or the like.

In one embodiment, a single long breath and/or a cessation of breathing are predefined features that the respiration module 320 detects in the respiration data of the individual 102. In a further embodiment, rapid or labored breathing is a predefined feature that the respiration module 320 detects in the respiration data of the individual 102. In another embodiment, rapid, labored breathing following a single long breath or a cessation of breathing is a predefined feature that the respiration module 320 detects in the respiration data of the individual 102. In a further embodiment, the respiration module 320 detects additional predefined features in the respiration data of the individual 102 that are associated with a seizure or another medical condition. In one embodiment, the respiration module 320 assigns increasing weighted severity values to predefined features in respiration data above (or in some cases below) selected threshold value as the distance from the threshold value increases.

In one embodiment, the respiration module 320 takes the positive integral of a mean-subtracted respiration waveform for each breath to detect a single large breath, a breath of at least a predefined volume, or the like, which may be indicated by a predefined increase in the integrated respiration waveform, an amplitude of the integrated respiration waveform exceeding a predefined threshold, or the like. In a further embodiment, the respiration module 320 takes the positive integral of the respiration waveform from the respiration sensor 112 for a sliding time window to produce an envelope waveform to detect a predefined change in respiration rate, rapid, labored breathing, or the like. In a further embodiment, the respiration module 320 detects breath duration, breath amplitude, respiration rate, and/or other predefined features in the respiration data using the respiration waveform from the respiration sensor 112 directly. In one embodiment, predefined features in the respiration data from the respiration sensor 112 are a strong indicator of relatively mild seizures that may be difficult to detect using other types of sensors.

In one embodiment, the EMG module 322 detects one or more predefined features in data from an EMG sensor 112 that measures muscle activity in the individual 102. The EMG sensor 112, in one embodiment, includes several high-impedance EMG electrodes that measure electric activity of a muscle that is proportional to physical muscle activity. During a seizure, individuals 102 often experience increased muscle activity, rhythmic muscle activity, synchronous muscle activity in different muscle groups, and the like, which the EMG module 322, in various embodiments, detects. The EMG module 322, in one embodiment, detects one or more of a predefined change in magnitude of an integrated EMG waveform, a predefined increase in rhythmic muscle activity, a predefined increase in mean firing rate of a muscle, a predefined change in an accumulated EMG waveform within a predefined time window, a predefined decrease in signal energy of an EMG waveform preceding the predefined feature, or the like.

In one embodiment, the EMG module 322 integrates an EMG waveform in a sliding time window to produce an EMG envelope waveform and detects a predefined change in magnitude of the integrated EMG waveform as a predefined feature, a predefined decrease in signal energy preceding a different predefined feature, or the like. In another embodiment, the EMG module 322 performs a frequency domain analysis of data from the EMG sensor 112, using a Fourier transformation, a Laplace transform, a Z-transform, a spectrum analyzer, or the like to detect a predefined increase in rhythmic muscle activity as a predefined feature. During a seizure, in one embodiment, EMG pulses have a rhythm of around 5 Hz, because the rate of muscle contraction is limited to the maximum rate of calcium cycling, which is around about 5 Hz. The EMG module 322, in one embodiment, detects a rhythm of muscle contraction around 5 Hz (and/or a harmonic of 5 Hz) as a predefined feature. In another embodiment, the EMG module 322 detects other frequencies of rhythmic muscle contraction as a predefined feature.

In a further embodiment, the EMG module 322 detects one or more predefined features in EMG data from two or more EMG sensors 112 that measure muscle activity in opposing muscle groups. Opposing agonistic and antagonistic muscle groups, such as biceps and triceps or the like, often have synchronized behavior during a seizure, but typically do not have synchronized behavior during normal activity. In one embodiment, the one or more sensors 110, 112 include a first EMG sensor 110 and a second EMG sensor 112 that measure muscle activity in opposing agonistic and antagonistic muscle groups. In one embodiment, the EMG module 322 detects a predefined amount of temporal correlation between muscle activity in opposing muscle groups as a predefined feature. In a further embodiment, the EMG module 322 detects additional predefined features in the EMG data of the individual 102 that are associated with a seizure or another medical condition. In one embodiment, the EMG module 322 assigns increasing weighted severity values to predefined features in EMG data above (or in some cases below) selected threshold value as the distance from the threshold value increases.

In one embodiment, the skin conductivity module 324 detects one or more predefined features in skin conductivity data for the individual 102 from a skin conductivity sensor 112, such as a galvanic skin response ("GSR") sensor, or the like. The skin conductivity module 324, in one embodiment, detects a predefined increase in the skin conductivity of the individual 102 as a predefined feature. The skin conductivity of the individual 102, in one embodiment, may increase during a seizure or another medical condition due to increased sweating of the individual 102, or the like.

In one embodiment, the skin temperature module 326 detects one or more predefined features in skin temperature data for the individual 102 from a thermometer, a thermistor, an infrared skin temperature sensor, or another skin temperature sensor. In one embodiment, the skin temperature module 326 detects a predefined change in the skin temperature of the individual 102 as a predefined feature. A seizure or other medical condition in the individual 102 may cause an abnormal increase or decrease in skin temperature, which the skin temperature module 326 detects.

In one embodiment, the peripheral blood oxygen saturation module 328 detects one or more predefined features in peripheral blood oxygen saturation data for the individual 102 from a pulse oximeter 112 or other peripheral blood oxygen saturation sensor. Saturation of peripheral blood oxygen ("SpO2") often decreases during a seizure in an individual 102. The peripheral blood oxygen saturation module 328, in one embodiment, detects a predefined decrease in SpO2 of the individual 102 as a predefined feature.

In one embodiment, the audible noise module 330 detects a predefined audible vocalization by the individual 102 in data from an audible noise sensor 112, such as a microphone, a microphone array, or the like. An individual 102 often makes audible vocalizations, such as gasping, gargling, screaming, or the like during a seizure. The audible vocalizations of an individual 102 are often fairly consistent between different seizures. Sometimes an individual 102, particularly an individual 102 who experiences prodrome or aura, may vocalize words such as "help." In one embodiment, the audible noise module 330 is trained to differentiate audible vocalizations (or a pattern of audible vocalizations which may include one or more words) that the individual 102 makes during a seizure or other medical condition from other vocalizations, and to detect the audible vocalizations of a seizure or other medical condition as a predefined feature. In a further embodiment, the audible noise module 330 detects a predefined volume (i.e. loudness or amplitude) of audible vocalizations as a predefined feature.

In one embodiment, the body motion module 332 detects one or more predefined features in body motion data for the individual 102 from one or more body motion sensors 112, such as gyroscopes, accelerometers, gravity sensors, and the like. The one or more body motion sensors 112, in various embodiments, measure motion, acceleration, orientation, and the like of the individual 102. In one embodiment, the one or more body motion sensors 112 include a gyroscope that measures torso orientation of the individual 102.

In one embodiment, the body motion module 332 detects falling down, rocking back and forth, and/or other predefined body movements as predefined features of a seizure or another medical condition. In another embodiment, the body motion module 332 detects relative body orientation (e.g., supine, prone, etc.). In a further embodiment, the body motion module 332 uses body motion data to determine an estimated severity of a seizure, a likelihood of an adverse event during a seizure, or the like.

In one embodiment, the confirmation feature module 302 detects one or more additional predefined features associated with a seizure or another medical condition in data from one or more of the sensors 110, 112, in addition to the predefined feature detected by the feature detection module 204. The confirmation feature module 302, in one embodiment, may be substantially similar to the feature detection module 204, may be integrated with the feature detection module 204, or the like, and may detect substantially similar predefined features as those discussed above with regard to the feature detection module 204, the heart activity module 318, the respiration module 320, the EMG module 322, the skin conductivity module 324, the skin temperature module 326, the peripheral blood oxygen saturation module 328, the audible noise module 330, and/or the body motion module 332.

In one embodiment, the confirmation feature module 302 detects the one or more additional predefined features in data from a different sensor 110, 112 than a sensor 110, 112 from which the feature detection module 204 detects a first predefined feature. For example, in one embodiment, the feature detection module 204 detects a first predefined feature in heart activity data from a heart activity sensor 110 and the confirmation feature module 302 detects a second predefined feature in respiration data from a respiration sensor 112, an EMG sensor 112, or the like. In a further embodiment, a first predefined feature that the feature detection module 204 detects and/or one or more additional predefined features that the confirmation feature module 302 detects includes a combination of several predefined features. In a further embodiment, a predefined feature includes a weighted combination of several predefined features, a combination of weighted severity values associated with predefined features, or the like, that exceeds a predefined threshold value.

The alert module 206, in one embodiment, broadcasts an alert in response to the confirmation feature module 302 detecting one or more additional predefined features. In one embodiment, the alert module 206 broadcasts a single alert in response to the feature detection module 204 detecting a first feature and the confirmation feature module 302 detecting one or more confirming additional predefined features. In a further embodiment, the alert module 206 broadcasts an initial alert in response to the feature detection module 204 detecting a first predefined feature and the alert module 206 broadcasts an escalated alert in response to the confirmation feature module 302 detecting one or more additional predefined features, or the like. In another embodiment, the alert module 206 broadcasts an alert in response to a combination of weighted severity values of the first predefined feature and the one or more additional predefined features exceeding a predefined threshold.

The confirmation feature module 302, in one embodiment, combines or otherwise analyzes a combination of predefined features and/or weighted severity values using a statistical signal processing method to detect one or more additional predefined features. Examples of statistical signal processing methods include a Bayes classifier or other Bayesian methods, neural networks, decision trees, a principal component analysis ("PCA"), an independent component analysis ("ICA"), a hidden Markov model, changes in probability density functions, changes in probability distribution functions, changes in cumulative distribution functions, Nayman-Pearson signal detection, a minimum probability of error method, multiple hypothesis testing, matched filters, an estimator-correlator method, vector observations, and/or other statistical signal processing methods.

In one embodiment, the severity module 304 determines an estimated severity of a seizure or other medical condition in the individual 102. The severity module 304, in one embodiment, bases the estimated severity on a combination of weighted severity values associated with one or more predefined features detected in data for the individual 102 by the feature detection module 204 and/or the confirmation feature module 302. The alert module 206, in one embodiment, broadcasts an alert that includes information of the estimated severity.

In one embodiment, the adverse event module 306 detects a predefined adverse event feature in sensor data for the individual 102. The predefined adverse event feature is associated with an adverse event, such as a fall, an arrhythmia, respiratory distress, a cessation of breathing, a loss of consciousness, or the like. In one embodiment, the adverse event module 306 detects an adverse event feature that occurs in sensor data for the individual 102 during or following a seizure or other medical condition. In a further embodiment, the adverse event module 306 detects adverse event features that occur in sensor data for the individual 102 independent of a seizure, another medical condition, and associated predefined features. The alert module 206, in one embodiment, broadcasts an adverse event alert in response to the adverse event module 306 detecting a predefined adverse event feature. Examples of adverse event features, in one embodiment, include a predefined decrease in HRV for the individual, body motion sensor data indicating a fall or loss of consciousness, respiration data indicating a cessation of breathing, heart activity data indicating an arrhythmia, and the like.

In one embodiment, the feature personalization module 308 adjusts definitions of predefined features based on sensor data from one or more previous seizures or other medical conditions of the individual 102. The feature personalization module 308, in one embodiment, receives an indication from a user, such as the caregiver 128, that the individual 102 is experiencing a seizure or other medical condition, and the feature personalization module 308 adjusts definitions of predefined features based on sensor data from the one or more sensors 110, 112 during the seizure or other medical condition. In a further embodiment, the feature personalization module 308 adjusts definitions of predefined features based on baseline sensor data that the one or more sensors 110, 112 receive while the individual 102 is not experiencing a seizure and/or another medical condition. The feature personalization module 308, in one embodiment, increases the accuracy of seizure symptom detection by personalizing definitions of predefined features to the individual 102.

In one embodiment, the data capture module 310 stores at least a portion of sensor data from a sensor 110, 112 that is associated with a predefined feature that the feature detection module 204 and/or the confirmation feature module 302 detects. In a further embodiment, the data capture module 310 stores substantially all data from one or more of the sensors 110, 112 for a predefined window of time. The data capture module 310, in one embodiment, stores data in computer readable storage media, such as flash media, RAM, a hard disk drive, or the like, located with the controller 106, at the base station 116, at the caregiver receiver device 130, or the like.

In one embodiment, the activity state module 312 detects an activity state of the individual 102 and adjusts definitions for one or more predefined features based on the detected activity state. Examples of activity states, in one embodiment, include sleeping, eating, exercising, resting, high, low, and/or other activity states. In one embodiment, the activity state module 312 detects the activity state of the individual 102 based on sensor data from the one or more sensors 110, 112, for example, by detecting one or more predefined activity state features, or the like. In a further embodiment, the activity state module 312 receives input from a user, such as the individual 102, the caregiver 128, or the like, indicating a current activity state of the individual 102. In another embodiment, the activity state module 312 predicts an activity state of the individual 102 based on a history of previous activity states, or the like.

In one embodiment, the treatment module 314 dispenses a treatment to the individual 102 in response to the feature detection module 204 and/or the confirmation feature module 302 detecting one or more predefined features. The treatment module 314, in one embodiment, dispenses the treatment to the individual 102 from a treatment source or reservoir to the individual 102 using intravenous cannulation, intramuscular, subcutaneous, nasal cannulation, oral cannulation, or the like. In one embodiment, the alert module 206 alerts the caregiver 128, a doctor, a medical professional, a medical monitoring center, or the like and the treatment module 314 receives treatment confirmation from the alerted entity, confirming that the treatment module 314 may dispense the treatment, and the treatment module 314 dispenses the treatment in response to the treatment confirmation. The treatment module 314, in one embodiment, administers a treatment that includes a medicinal fluid or other machine administrable treatment. For example, the treatment module 314 may administer a medicinal treatment using a drug pump or the like, may administer an electrical treatment such as vagus nerve stimulation ("VNS") using an electrical stimulator, or the like. In certain embodiments, a treatment device such as a drug pump, an electrical stimulator, or the like may be wearable and/or implantable, and a securing article 104 may removably secure the treatment device to the individual 102. In another embodiment, the treatment module 314 dispenses a stimulus such as a vibration, sound, or mild electrical stimulus in response to the adverse event module 306 determining that the individual 102 appears to be unconscious.

In one embodiment, the location module 316 determines a location of the individual 102. The alert module 206, in a further embodiment, includes the location of the individual 102 in an alert, allowing the caregiver 128 or another alerted entity to locate the individual 102. The location module 316, in one embodiment, determines the location of the individual 102 using a global positioning system ("GPS") device or other global navigation satellite system, wireless communications triangulation, an indoor positioning system, or the like.

Figure 4A:
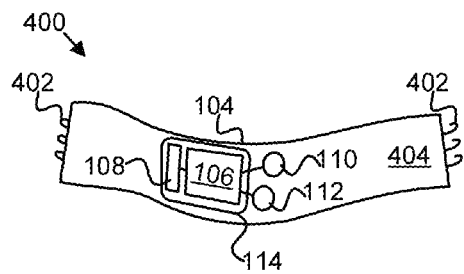
FIG. 4A is a schematic block diagram illustrating one embodiment of a securing article in accordance with the present invention.

FIG. 4A depicts one embodiment 400 of the securing article 104. In the depicted embodiment 400, the securing article 104 includes a wearable strap 404 coupled to the controller 106, the power storage device 108, the housing 114, and the one or more sensors 110, 112. In other embodiments, the one or more sensors 110, 112 may be coupled to the wearable strap 404, and one or more of the controller 106, the power storage device 108, the housing 114, and the like may be located elsewhere. The securing article 104, in the depicted embodiment 400, further includes one or more fasteners 402. The one or more fasteners 402, in the depicted embodiment 400, include hook and loop fasteners. In other embodiments, the one or more fasteners 402 may include Velcro™ type hook and loop fasteners, buttons, buckles, clasps, snaps, adhesives, clips, zippers, and/or another type of fastener. The wearable strap 404, in various embodiments, is designed for the individual 102 to wear the strap around the torso, around an arm, around a wrist, around a leg, around an ankle, or the like.

The one or more sensors 110, 112, in one embodiment, are coupled to the wearable strap 404 using one or more fasteners, adhesives, or the like. In a further embodiment, the one or more sensors 110, 112 are integrated with the wearable strap 404. For example, the one or more sensors 110, 112 may include smart textile or other conductive fabric that conducts electrical signals between the one or more sensors 110, 112 and the controller 106; the one or more sensors 110, 112 may include carbon-impregnated nylon, metallic fibers, graphite fibers, or the like embedded in the wearable strap 404; or the one or more sensors 110, 112 may otherwise be integrated with the wearable strap 404.

Figure 4B:
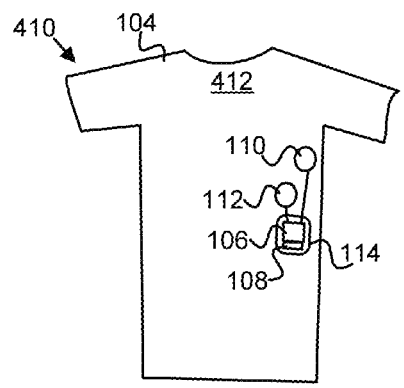
FIG. 4B is a schematic block diagram illustrating another embodiment of a securing article in accordance with the present invention.

FIG. 4B depicts another embodiment 410 of the securing article 104. In the depicted embodiment 410, the securing article 104 includes an article of clothing 412, a shirt, to which the controller 106, the power storage device 108, the housing 114, and the one or more sensors 110, 112 are coupled. In other embodiments, the one or more sensors 110, 112 may be coupled to the article of clothing 412, and one or more of the controller 106, the power storage device 108, the housing 114, and the like may be located elsewhere. The article of clothing 412, in other embodiments, may include pants, a sock, a glove, a headband, a hat, an undergarment, a shoe, or the like.

The one or more sensors 110, 112, in one embodiment, are coupled to the article of clothing 412 using one or more fasteners, adhesives, or the like. In a further embodiment, the one or more sensors 110, 112 are integrated with the article of clothing 412. For example, the one or more sensors 110, 112 may include smart textile or other conductive fabric that conducts electrical signals between the one or more sensors 110, 112 and the controller 106; the one or more sensors 110, 112 may include carbon-impregnated nylon, metallic fibers, graphite fibers, or the like embedded in the article of clothing 412; or the one or more sensors 110, 112 may otherwise be integrated with the article of clothing 412.

Figure 4C:
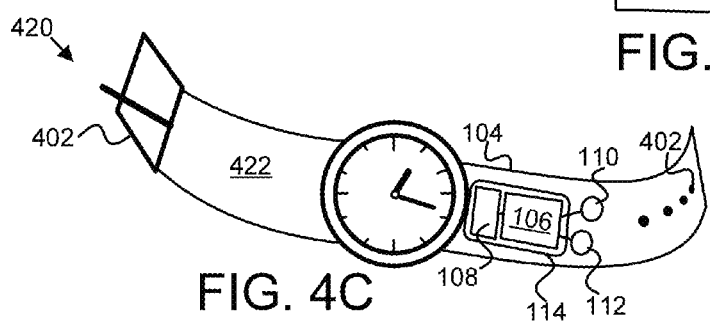
FIG. 4C is a schematic block diagram illustrating a further embodiment of a securing article in accordance with the present invention.

FIG. 4C depicts a further embodiment of the securing article 104. In the depicted embodiment 420, the securing article 104 includes an article of jewelry 422, a watch, to which the controller 106, the power storage device 108, the housing 114, and the one or more sensors 110, 112 are coupled. In other embodiments, the one or more sensors 110, 112 may be coupled to the article of jewelry 422, and one or more of the controller 106, the power storage device 108, the housing 114, and the like may be located elsewhere. The securing article 104, in the depicted embodiment 400, further includes one or more fasteners 402. The one or more fasteners 402, in the depicted embodiment 400, include a buckle. The article of jewelry 422, in the depicted embodiment, is designed for the individual 102 to wear around a wrist. In other embodiments, the article of jewelry 422 may include a bracelet, a necklace, an anklet, a belt, a ring, or the like to be worn around the neck, around a finger, around an ankle, around the waist, or the like.

The one or more sensors 110, 112, in one embodiment, are coupled to the article of jewelry 422 using one or more fasteners, adhesives, or the like. In a further embodiment, the one or more sensors 110, 112 are integrated with the article of jewelry 422. For example, the one or more sensors 110, 112 may include smart textile or other conductive fabric that conducts electrical signals between the one or more sensors 110, 112 and the controller 106; the one or more sensors 110, 112 may include carbon-impregnated nylon, metallic fibers, graphite fibers, or the like embedded in the article of jewelry 422; or the one or more sensors 110, 112 may otherwise be integrated with the article of jewelry 422.

Figure 4D:
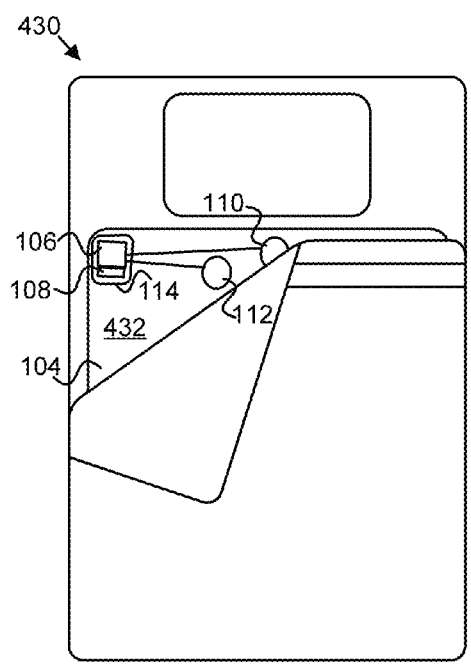
FIG. 4D is a schematic block diagram illustrating an additional embodiment of a securing article in accordance with the present invention.

FIG. 4D depicts an additional embodiment of the securing article 104. In the depicted embodiment 430, the securing article 104 includes a bedding layer 432 to which the controller 106, the power storage device 108, the housing 114, and the one or more sensors 110, 112 are coupled. In other embodiments, the one or more sensors 110, 112 may be coupled to the bedding layer 432, and one or more of the controller 106, the power storage device 108, the housing 114, and the like may be located elsewhere. The bedding layer 432, in the depicted embodiment, is a bedding pad. In other embodiments, the bedding layer 432 may include a sheet, a blanket, a pillow case, or another type of bedding layer.

The one or more sensors 110, 112, in one embodiment, are coupled to the bedding layer 432 using one or more fasteners, adhesives, or the like. In a further embodiment, the one or more sensors 110, 112 are integrated with the bedding layer 432. For example, the one or more sensors 110, 112 may include smart textile or other conductive fabric that conducts electrical signals between the one or more sensors 110, 112 and the controller 106; the one or more sensors 110, 112 may include carbon-impregnated nylon, metallic fibers, graphite fibers, or the like embedded in the bedding layer 432; or the one or more sensors 110, 112 may otherwise be integrated with the bedding layer 432.

Figure 4E:
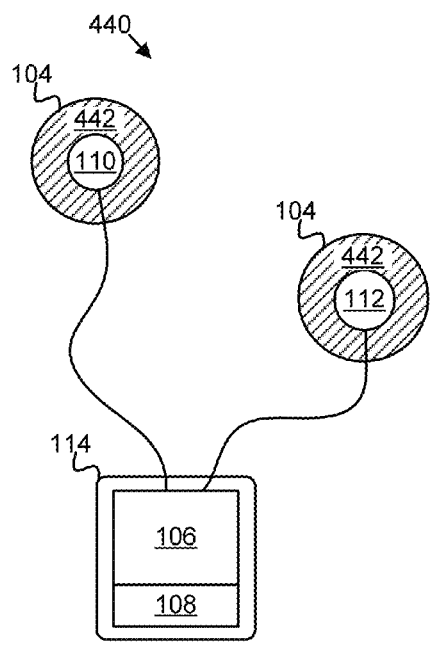
FIG. 4E is a schematic block diagram illustrating one more embodiment of a securing article in accordance with the present invention.

FIG. 4E depicts one more embodiment of the securing article 104. In the depicted embodiment 440, the securing article 104 includes one or more adhesive bandages 442 that affix the one or more sensors 110, 112 to the individual 102. The one or more adhesive bandages 442, in one embodiment, are disposable and replaceable. The one or more adhesive bandages 442, in one embodiment, stick directly to the skin of the individual 102, to place the one or more sensors 110, 112 in contact with the skin of the individual 102. In a further embodiment, the one or more adhesive bandages 442 wrap around the individual 102 and stick to themselves to place the one or more sensors 110, 112 in proximity to the individual 102. For example, in various embodiments, an adhesive bandage 442 may be designed to wrap around a finger, a toe, the torso, an arm, a wrist, a leg, an ankle, or the like of the individual 102 and to removably engage an opposite end of the adhesive bandage 442 to one or more of the sensors 110, 112 to the individual 102.

Figure 5A:
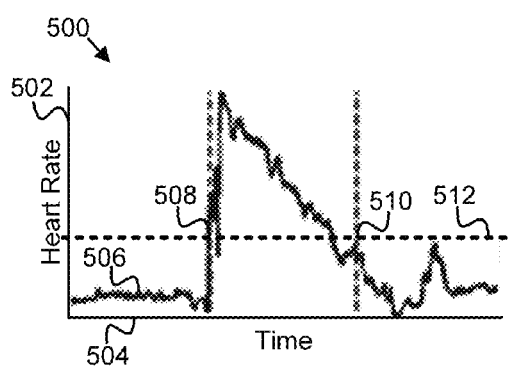
FIG. 5A is a schematic block diagram illustrating one embodiment of a predefined feature in accordance with the present invention.

FIG. 5A depicts one embodiment of a predefined feature 500. The depicted embodiment includes data 506 graphically representing a heart rate 502 of the individual 102, the vertical axis of the data 506, in relation to time 504, the horizontal axis of the data 506. The sensor module 202, in one embodiment, receives the data 506 of the heart rate 502, or corresponding heart activity data, from a heart activity sensor 110.

In the depicted embodiment, the predefined feature 500 is a heart rate 502 above a predefined threshold 512. The data 506, in the depicted embodiment, rises above the predefined threshold 512 at a time 504 around about a beginning 508 of a seizure or other medical condition, and falls below the predefined threshold 512 at a time 504 around about an end 510 of the seizure or other medical condition. The feature detection module 204, in one embodiment, detects the predefined feature 500 in the data 506, and the alert module 206 broadcasts an alert in response to the feature detection module 204 detecting the predefined feature 500.

Figure 5B:
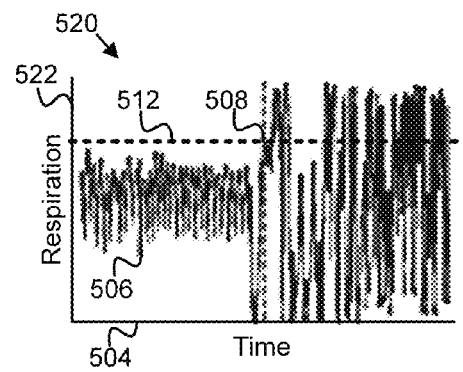
FIG. 5B is a schematic block diagram illustrating another embodiment of a predefined feature in accordance with the present invention.

FIG. 5B depicts another embodiment of a predefined feature 520. The depicted embodiment includes data 506 graphically representing respiration 522, the vertical axis of the data 506, in relation to time 504, the horizontal axis of the data 506. Respiration 522 may include respiration volume, respiration amplitude, or another indicator of respiration of the individual 102. The sensor module 202, in one embodiment, receives the data 506 of respiration 522 from a respiration sensor 112.

In the depicted embodiment, the predefined feature 520 is a volume, amplitude, or other indicator of respiration 522 above a predefined threshold 512. The data 506, in the depicted embodiment, rises above the predefined threshold 512 at a time 504 around about a beginning 508 of a seizure or other medical condition. The feature detection module 204, in one embodiment, detects the predefined feature 520 in the data 506, and the alert module 206 broadcasts an alert in response to the feature detection module 204 detecting the predefined feature 520.

Figure 5C:
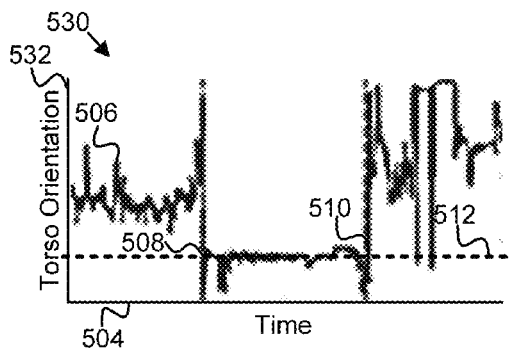
FIG. 5C is a schematic block diagram illustrating a further embodiment of a predefined feature in accordance with the present invention.

FIG. 5C depicts a further embodiment of a predefined feature 530. The depicted embodiment includes data 506 graphically representing torso orientation 532 or another indicator of body motion, the vertical axis of the data 506, in relation to time 504, the horizontal axis of the data 506. The sensor module 202, in one embodiment, receives the data 506 of the torso orientation 532 of the individual 102, or corresponding body motion data, from a body motion sensor 112.

In the depicted embodiment, the predefined feature 530 is a predefined torso orientation 532, represented by a torso orientation 532 rapidly falling below a predefined threshold 512. The data 506, in the depicted embodiment, falls below the predefined threshold 512 at a time 504 around about a beginning 508 of a seizure or other medical condition, which may correspond to the individual 102 falling down or the like. The feature detection module 204, in one embodiment, detects the predefined feature 530 in the data 506, and the alert module 206 broadcasts an alert in response to the feature detection module 204 detecting the predefined feature 530. In a further embodiment, the severity module 304 and/or the adverse event module 306 use the predefined event 530 corresponding to torso orientation 532 or another indicator of body motion to determine a severity of a seizure or other medical condition, to detect symptoms of an adverse event such as a fall, or the like.

Figure 5D:
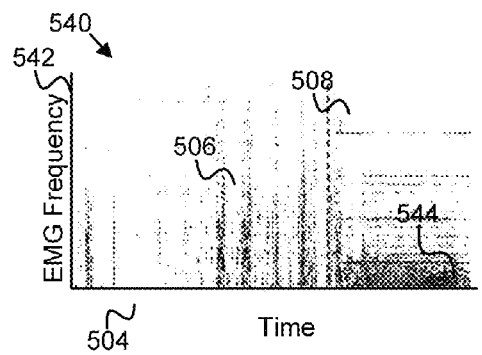
FIG. 5D is a schematic block diagram illustrating an additional embodiment of a predefined feature in accordance with the present invention.

FIG. 5D depicts an additional embodiment of a predefined feature 540. The depicted embodiment includes data 506 graphically representing a frequency 542 of EMG data, the vertical axis of the data 506, in relation to time 504, the horizontal axis of the data 506. The EMG module 322, in one embodiment, transforms EMG data from an EMG sensor 112 to the frequency domain to obtain the data 506.

In the depicted embodiment, the predefined feature 540 is horizontal banding 544 in the data 506 around one or more frequencies 542, such as 5 Hz, harmonics of 5 Hz, or the like. The data 506, in the depicted embodiment, prior to the beginning 508 of a seizure or other medical condition, is relatively evenly spread across frequencies 542. The data 506, in the depicted embodiment, begins banding around one or more frequencies 542 forming horizontal bands 544 at a time 504 around about the beginning 508 of a seizure or other medical condition. The feature detection module 204, in one embodiment, detects the predefined feature 540, the horizontal banding 544 around one or more frequencies 542, in the data 506, and the alert module 206 broadcasts an alert in response to the feature detection module 204 detecting the predefined feature 540.

Figure 6:
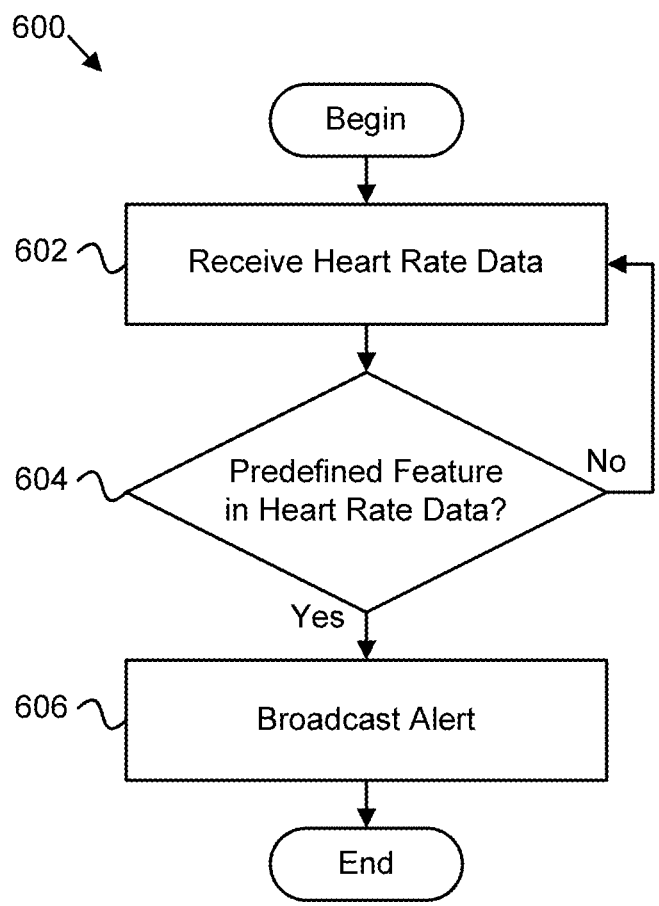
FIG. 6 is a schematic flow chart diagram illustrating one embodiment of a method for seizure symptom detection in accordance with the present invention.

FIG. 6 depicts one embodiment of a method 600 for seizure symptom detection. In the depicted embodiment, the method 600 begins, and the sensor module 202 receives 602 heart activity data for the individual 102 from a heart activity sensor 110. In a further embodiment, the sensor module 202 may receive 602 other physiological data for the individual 102 from one or more additional sensors 112.

The feature detection module 204, in the depicted embodiment, detects 604 whether there is a predefined feature in the heart activity data, in other physiological data of the individual 102, or the like. If the feature detection module 204 detects 604 a predefined feature in the heart activity data, the alert module 206 broadcasts 606 an alert and the method 600 ends. If the feature detection module 204 does not detect 604 a predefined feature in the heart activity data, the method 600 returns to the receiving step 602, the sensor module 202 continues to receive 602 heart activity data from the heart activity sensor 110, and the feature detection module 204 continues to detect 604 predefined features in the heart activity data.

Figure 7:
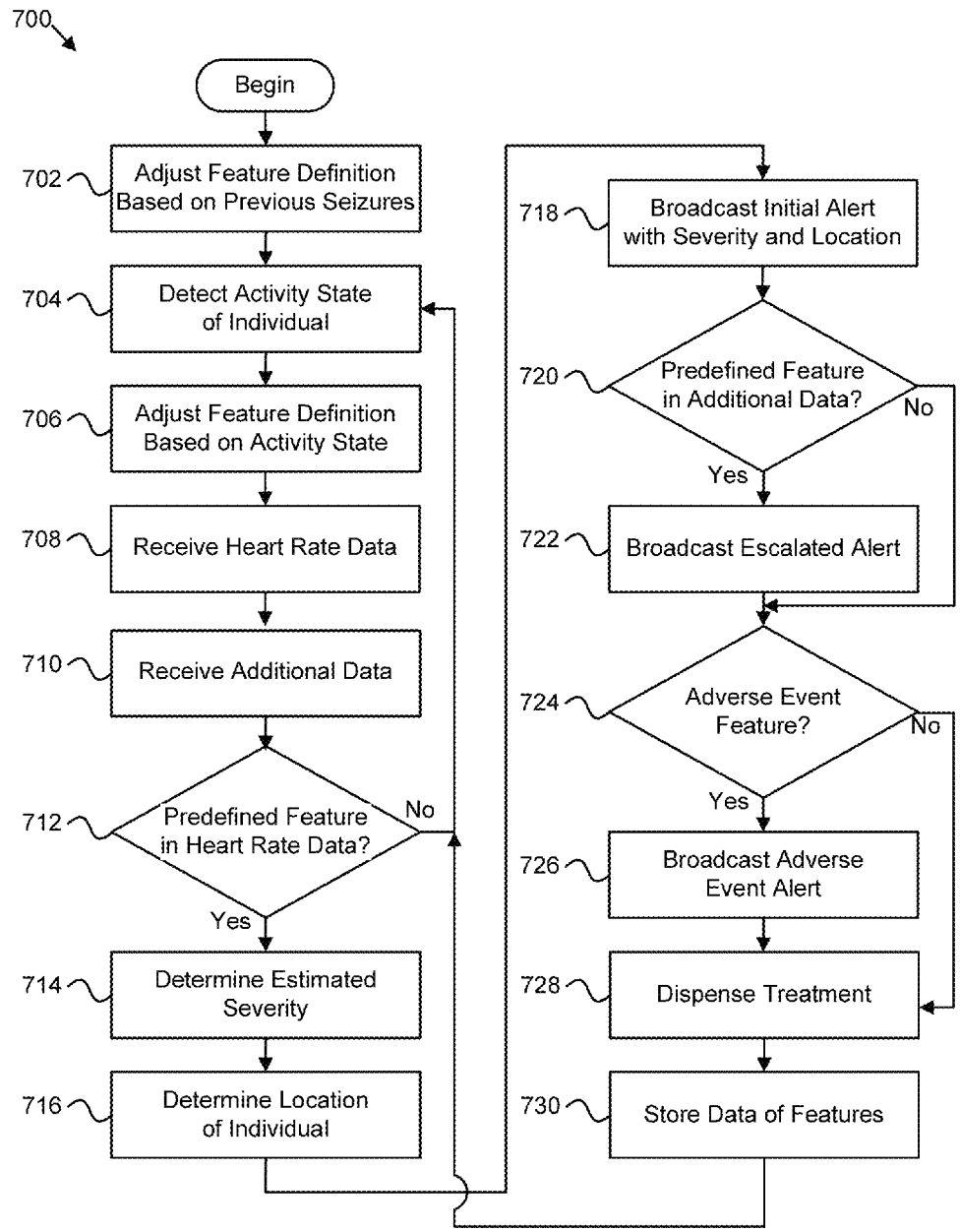
FIG. 7 is a schematic flow chart diagram illustrating another embodiment of a method for seizure symptom detection in accordance with the present invention.

FIG. 7 depicts another embodiment of a method 700 for seizure symptom detection. In the depicted embodiment, the method 700 begins, and the feature personalization module 308 adjusts 702 one or more definitions of predefined features based on previous seizures of the individual 102. The activity state module 312 detects 704 an activity state of the individual 102 and adjusts 706 one or more definitions of predefined features based on the detected 704 activity state. The sensor module 202, in the depicted embodiment, receives 708 heart activity data for the individual 102 from a heart activity sensor 110, and the sensor module 202 receives 710 additional data for the individual 102 from one or more additional sensors 112. In one embodiment, the method 700 continues to perform the detecting step 704, the adjusting step 706, the receiving step 708, the receiving step 710, and/or other steps in the method 700 throughout execution of the method 700.

The feature detection module 204 detects 712 whether there is a predefined feature in the heart activity data. If the feature detection module 204 detects 712 a predefined feature in the heart activity data, the severity module 304 determines 714 an estimated severity of the seizure or other medical condition based on the received 708 heart activity data and/or the received 710 additional data. The location module 316 determines 716 a location of the individual 102, and the alert module 206 broadcasts 718 an initial alert that includes the estimated severity and the location of the individual 102. If the feature detection module 204 does not detect 712 a predefined feature in the heart activity data, the method 700 returns to the detecting step 704 and the method 700 continues.

The confirmation feature module 302, in the depicted embodiment, detects 720 whether there are one or more additional predefined features in the received 710 additional data from the one or more additional sensors 112. If the confirmation feature module 302 detects 720 one or more additional predefined features in the additional data, the alert module 206 broadcasts 722 an escalated alert. In another embodiment, the alert module 206 does not broadcast 718 the initial alert, but instead broadcasts 722 just the escalated alert, and may include the estimated severity and the location of the individual 103 in the escalated alert. If the confirmation feature module 302 does not detect 720 one or more additional predefined features, the alert module 206 does not broadcast 722 the escalated alert.

The adverse event module 306, in the depicted embodiment, detects 724 whether there is an adverse event feature in the received 708 heart activity data and/or in the received 710 additional data. If the adverse event module 306 detects 724 an adverse event feature, the alert module 206 broadcasts 726 an adverse event alert. If the adverse event module 306 does not detect 724 an adverse event feature, the alert module 206 does not broadcast 726 the adverse event alert.

The treatment module 314, in the depicted embodiment dispenses 728 a treatment to the individual 102. In the depicted embodiment, the data capture module 310 stores 730 at least a portion of the data received 708 from the heart activity sensor 110 and/or received 710 from the one or more additional sensors 112. In one embodiment, the data capture module 310 stores 730 data corresponding to a detected 712 predefined feature, one or more detected 720 additional predefined features, a detected 724 adverse event feature, or the like. The method 700 returns to the detecting step 704 and the method continues.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to detect seizure symptoms, the apparatus comprising:
  a sensor module that receives heart activity data for an individual from a heart activity sensor and that receives additional data from one or more additional sensors, the one or more additional sensors comprising one or more of:
    a respiration sensor that receives respiration activity from the individual;
    an electromyography ("EMG") sensor measures electric activity of one or more muscles of the individual;
    a skin conductivity sensor that measures skin conductivity of the individual;

a skin temperature sensor that measures skin temperature of the individual;

a peripheral blood oxygen saturation sensor that measures saturation of peripheral blood oxygen of the individual; and an audible noise sensor that measures audible vocalizations of the individual;

a feature detection module that detects a predefined feature in the heart activity data, the predefined feature associated with a seizure;

a confirmation feature module that, in response to the feature detection module detecting a predefined feature in the heart rate activity, detects one or more additional predefined features associated with a seizure in additional data for the individual from the one or more additional sensors; and an alert module that broadcasts an alert in response to the feature detection module detecting the predefined feature and the confirmation feature module detecting at least one additional predefined feature.

2. The apparatus of claim 1, wherein the one or more additional predefined features comprise one or more of a predefined increase in an integrated respiration waveform, a predefined increase in respiration amplitude, a predefined change in respiration rate, a breath of at least a predefined duration, a breath of at least a predefined amplitude, a breath of at least a predefined volume, and a predefined change in a period of a respiration interval.

3. The apparatus of claim 1, wherein the one or more additional predefined features comprise one or more of a predefined change in magnitude of an integrated EMG waveform, a predefined increase in rhythmic muscle activity, a predefined increase in mean firing rate of a muscle, a predefined change in an accumulated EMG waveform within a predefined time window, and a predefined decrease in signal energy of an EMG waveform preceding the predefined feature.

4. The apparatus of claim 3, wherein the one or more additional sensors further include an opposing EMG sensor, the EMG sensor measuring muscle activity in a first muscle group and the opposing EMG sensor measuring muscle activity in an opposing muscle group, wherein the one or more additional predefined features comprise a predefined amount of correlation between muscle activity in the first muscle group and in the opposing muscle group.

5. The apparatus of claim 1, wherein the one or more additional features comprise one or more of:
a predefined increase in a skin conductivity of the individual;
a predefined change in a skin temperature of the individual;
a predefined decrease in a peripheral blood oxygen level of the individual; and
a predefined audible vocalization by the individual.

6. The apparatus of claim 1, further comprising a severity module that determines an estimated severity of a seizure in the individual based on a combination of a weighted severity value associated with the predefined feature and one or more weighted severity values associated with the one or more additional predefined features, the alert comprising information of the estimated severity.

7. The apparatus of claim 6, wherein the one or more additional sensors include a body motion sensor that measures at least one of motion and orientation of the individual, the severity module basing the estimated severity of a seizure in the individual at least partially on input from the body motion sensor, the body motion sensor selected from the group consisting of a gyroscope and an accelerometer.

8. The apparatus of claim 1, further comprising an adverse event module that detects a predefined adverse event feature in at least one of the heart activity data and the data from the one or more additional sensors, the predefined adverse event feature associated with an adverse event, the adverse event selected from the group consisting of a fall, an arrhythmia, respiratory distress, a cessation of breathing, and a loss of consciousness, the alert module broadcasting an adverse event alert in response to the adverse event module detecting the predefined adverse event feature.

9. The apparatus of claim 1, wherein the alert module broadcasts an initial alert in response to the feature detection module detecting the predefined feature and broadcasts an escalated alert in response to the confirmation feature module detecting the one or more additional predefined features.

10. The apparatus of claim 1, wherein the alert that the alert module broadcasts is selected from the group comprising an audible alert, a broadcast signal to a caregiver receiver device, and a telephonic communication to a medical monitoring center.

11. The apparatus of claim 1, further comprising a feature personalization module that adjusts a definition of the predefined feature based on heart activity data from one or more previous seizures of the individual.

12. The apparatus of claim 1, further comprising a data capture module that stores at least the heart activity data associated with the predefined feature.

13. The apparatus of claim 1, further comprising an activity state module that detects an activity state of the individual and adjusts a definition of the predefined feature based on the detected activity state.

14. The apparatus of claim 1, wherein the predefined feature is selected from the group consisting of heart activity outside of predefined heart activity threshold values, a predefined change in heart activity, and a predefined decrease in heart rate variability.

15. The apparatus of claim 1, further comprising a treatment module that dispenses a treatment to the individual in response to the feature detection module detecting the predefined feature.

16. The apparatus of claim 1, further comprising a location module that determines a location of the individual, wherein the alert comprises information of the location of the individual.

17. A system to detect seizure symptoms, the system comprising:
a heart activity sensor that measures heart activity of an individual;
a securing article that removably places the heart activity sensor in proximity to the individual; and
a controller comprising,
a sensor module that receives heart activity data for the individual from the heart activity sensor and that receives additional data from one or more additional sensors, the one or more additional sensors comprising one or more of:
a respiration sensor that receives respiration activity from the individual;
an electromyography ("EMG") sensor measures electric activity of one or more muscles of the individual;
a skin conductivity sensor that measures skin conductivity of the individual;
a skin temperature sensor that measures skin temperature of the individual;

a peripheral blood oxygen saturation sensor that measures saturation of peripheral blood oxygen of the individual; and an audible noise sensor that measures audible vocalizations of the individual;

a feature detection module that detects a predefined feature in the heart activity data, the predefined feature associated with a seizure;

a confirmation feature module that, in response to the feature detection module detecting a predefined feature in the heart rate activity, detects one or more additional predefined features associated with a seizure in additional data for the individual from the one or more additional sensors; and an alert module that broadcasts an alert in response to the feature detection module detecting the predefined feature and the confirmation feature module detecting at least one additional predefined feature.

18. The system of claim 17, the securing article removably placing the one of more additional sensors in proximity to the individual.

19. The system of claim 17, further comprising a caregiver receiver device that receives the alert from the alert module.

20. The system of claim 17, further comprising a base unit device that performs one or more steps selected from the group consisting of storing at least a portion of the heart activity data, visually displaying at least a portion of the heart activity data, and sending at least a portion of the heart activity data to a remote device.

21. The system of claim 17, further comprising a power storage device coupled to the securing article, the power storage device providing electric power to at least one of the heart activity sensor and the controller.

22. The system of claim 17, wherein the securing article is selected from the group consisting of a wearable strap coupled to the heart activity sensor, an article of clothing to which the heart activity sensor is coupled, an article of jewelry to which the heart activity sensor is coupled, a bedding layer to which the heart activity sensor is coupled, an adhesive bandage that affixes the heart activity sensor to the individual, and an implanted device implanting the heart activity sensor within the individual.

23. The system of claim 17, wherein the controller is coupled to the securing article.

24. A method for detecting seizure symptoms, the method comprising:

receiving heart activity data for an individual from a heart activity sensor and receiving additional data from one or more additional sensors, the one or more additional sensors comprising one or more of:

a respiration sensor that receives respiration activity from the individual;

an electromyography ("EMG") sensor measures electric activity of one or more muscles of the individual;

a skin conductivity sensor that measures skin conductivity of the individual;

a skin temperature sensor that measures skin temperature of the individual;

a peripheral blood oxygen saturation sensor that measures saturation of peripheral blood oxygen of the individual; and an audible noise sensor that measures audible vocalizations of the individual;

detecting a predefined feature in the heart activity data, the predefined feature associated with a seizure;

detecting one or more additional predefined features associated with a seizure in additional data for the individual from the one or more additional sensors, in response to detecting the predefined feature in the heart rate activity; and broadcasting an alert in response to detecting the predefined feature and detecting at lease one additional predefined feature.

25. The method of claim 24, further comprising determining an estimated severity of a seizure in the individual based on a combination of a weighted severity value associated with the predefined feature and one or more weighted severity values associated with the one or more additional predefined features, the alert comprising information of the estimated severity.

26. The method of claim 24, further comprising, detecting a predefined adverse event feature in at least one of the heart activity data and the additional data from the one or more additional sensors, the predefined adverse event feature associated with an adverse event, the adverse event selected from the group consisting of a fall, respiratory distress, an arrhythmia, a cessation of breathing, and a loss of consciousness; and broadcasting an adverse event alert in response to detecting the predefined adverse event feature.

27. The method of claim 24, further comprising adjusting a definition of the predefined feature based on heart activity data from one or more previous seizures of the individual.

28. The method of claim 24, further comprising, detecting an activity state of the individual; and adjusting a definition of the predefined feature based on the detected activity state.

* * * * *